United States Patent [19]
Tucker

[11] Patent Number: 5,895,412
[45] Date of Patent: Apr. 20, 1999

[54] DEVICE AND METHOD FOR SEALING TISSUE

[75] Inventor: Robert Tucker, North Liberty, Iowa

[73] Assignee: Fusion Medical Technologies, Inc., Mountain View, Calif.

[21] Appl. No.: 08/850,549

[22] Filed: May 2, 1997

Related U.S. Application Data

[63] Continuation of application No. 08/542,199, Oct. 11, 1995, abandoned.

[51] Int. Cl.$^6$ ...................................... A61B 17/08
[52] U.S. Cl. ........................... 606/215; 606/213; 606/214
[58] Field of Search ........................... 606/214, 215, 606/216, 213; 222/146.5; 525/54.1; 424/450

[56] References Cited

U.S. PATENT DOCUMENTS

| | | |
|---|---|---|
| 3,563,228 | 2/1971 | Seiderman . |
| 3,810,473 | 5/1974 | Cruz et al. . |
| 3,937,223 | 2/1976 | Roth . |
| 4,034,750 | 7/1977 | Seiderman . |
| 4,038,519 | 7/1977 | Foucras .................... 604/114 |
| 4,122,850 | 10/1978 | Bucalo .................... 604/114 |
| 4,265,618 | 5/1981 | Herskovitz et al. .................... 604/114 |
| 4,382,441 | 5/1983 | Svedman .................... 604/114 |
| 4,465,478 | 8/1984 | Sabelman et al. . |
| 4,470,415 | 9/1984 | Wozniak . |
| 4,672,969 | 6/1987 | Dew . |
| 4,699,186 | 10/1987 | Palin et al. . |
| 4,743,229 | 5/1988 | Chu . |
| 4,793,807 | 12/1988 | Friedman et al. .................... 433/80 |
| 4,854,320 | 8/1989 | Dew et al. . |
| 4,931,546 | 6/1990 | Tardy et al. . |
| 5,071,417 | 12/1991 | Sinofsky . |
| 5,140,984 | 8/1992 | Dew et al. . |
| 5,147,203 | 9/1992 | Seidenberg . |
| 5,156,613 | 10/1992 | Sawyer . |
| 5,201,745 | 4/1993 | Tayot et al. . |
| 5,207,670 | 5/1993 | Sinofsky .................... 606/8 |
| 5,209,776 | 5/1993 | Bass et al. . |
| 5,219,328 | 6/1993 | Morse et al. .................... 606/214 |
| 5,324,305 | 6/1994 | Kanner .................... 606/213 |
| 5,328,955 | 7/1994 | Rhee et al. .................... 525/54.1 |
| 5,372,585 | 12/1994 | Tiefenbrun et al. .................... 606/213 |
| 5,436,135 | 7/1995 | Tayot et al. . |
| 5,469,867 | 11/1995 | Schmitt .................... 128/898 |
| 5,529,577 | 6/1996 | Hammerslag .................... 606/214 |
| 5,540,677 | 7/1996 | Sinofsky .................... 606/213 |
| 5,607,694 | 3/1997 | Marx .................... 424/450 |
| 5,614,587 | 3/1997 | Rhee et al. .................... 525/54.1 |

FOREIGN PATENT DOCUMENTS

| | | |
|---|---|---|
| 9316687 | 9/1993 | WIPO . |
| 9317669 | 9/1993 | WIPO . |
| 9421324 | 9/1994 | WIPO . |
| 9424962 | 11/1994 | WIPO . |
| 9509883 | 4/1995 | WIPO . |

*Primary Examiner*—Michael Buiz
*Assistant Examiner*—Julian W. Woo
*Attorney, Agent, or Firm*—Townsend and Townsend and Crew LLP

[57] ABSTRACT

An apparatus and method for effecting and enhancing wound closure in tissue is disclosed. Wounds and tissue are sealed by heating a sealant material, such as collagen, in an applicator (10) to a temperature sufficient to melt the sealant. The melted sealant is then extruded through a distal tip of an elongate shaft (22) and applied to the target site, where it cools and sets to form bonds with the underlying tissue. The heated sealant flows over the wound to create an effective barrier against further blood leakage and, upon cooling, it readily adheres to the tissue to seal the wound. In addition, since high intensity energy is not applied directly to the wound, damage or destruction of neighboring tissue is minimized.

58 Claims, 3 Drawing Sheets

DEVICE AND METHOD FOR SEALING TISSUE

This is a Continuation of application Ser. No. 08/542,199, filed Oct. 11, 1995, now abandoned, the disclosure of which is incorporated by reference.

BACKGROUND OF THE INVENTION

1. Field of the Invention

The present invention relates generally to devices, articles, and methods for effecting and enhancing wound closure in tissue. More particularly, the present invention relates to a method and apparatus for heating a sealant material and applying the heated sealant to tissue to close wounds and to join severed vessels.

Most surgical disciplines are concerned with the repair of damaged tissues and vessels. Tissue damage can be the result of direct trauma to the body or as part of a surgical procedure in which there is a separation of normally continuous tissue such as blood vessels. Historically, suturing has been the accepted technique for rejoining severed tissues and closing wounds. To suture a wound, the surgeon manually stitches the surrounding tissue with a surgical needle and suturing thread, and more recently, with a variety of polymeric or metallic staples.

While suturing and stapling techniques are often successful, there are a number of limitations inherent in such mechanical approaches. The practice of suturing or stapling tissue together not only requires significant skill, but is a relatively slow process, particularly when extensive repair is required or when anastomosing tiny biological structures. Even when suturing is properly performed, however, this technique can be less than satisfactory because of the gaps which are left between the stitches and the possibility of progressive structural weakening over time. For example, the gaps leave the wound open to bacteria, producing a risk of infection. In addition, the suture needle or staples puncture the tissue, producing holes through which biological fluid may leak.

In an effort to overcome the difficulties associated with conventional suturing techniques, sutureless repairs using surgical adhesives or glues have been developed. These surgical adhesives adhere to tissue surfaces and form a bond until the tissue heals. For example, one common tissue adhesive is fibrin adhesive or glue typically containing a concentrate of fibrinogen and thrombin. These agents are mixed together to form a clot joining separated tissues, forming a biocompatible bond therebetween. Fibrin adhesive, however, is usually obtained from pooled human plasma and the threat of infection from agents such as Hepatitis "B", HIV virus or others has outweighed the benefits of obtaining commercial quantities of fibrin adhesive. Non-biological materials, such as isobutyl-2-cyanoacrylate, have also been examined as potential surgical adhesives. These materials, however, are generally irritating to tissues, difficult to apply and often fail to form a permanent closure.

In another approach, electrosurgical, cauterization and cryogenic techniques have been developed to reduce the flow of blood in a wound or a surgically-induced incision. Electrosurgical procedures, either monopolar or bipolar, usually operate through the application of very high frequency currents to cut or ablate tissue structures. Cauterization involves using intense heat to sear and seal the open ends of the tissue. This heat can be generated by a variety of different methods, such as resistance heating of a metallic probe. Cryogenic techniques involve applying a cryogenic temperature to freeze the tissue, thereby discontinuing undesired blood flow. These electrosurgical, cauterization and cryogenic techniques, however, may damage or destroy the surrounding tissue leading to longer healing times, infection and scarring. Electrosurgical techniques, particularly monopolar procedures, also create the potential danger that the electric current will flow through undefined paths in the patient's body, thereby increasing the risk of unwanted electrical stimulation to portions of the patient's body.

More recently, lasers have been utilized to controllably generate high intensity optical energy that is absorbed by the damaged tissue. The heat produced by absorption of the optical energy converts biological tissue into a denatured proteinaceous substance which forms a biological glue that closes the wound. Similar to cauterization techniques, however, the high intensity optical energy in this procedure creates a substantial risk of damaging neighboring tissues.

For these and other reasons, it would be desirable to provide procedures for effectively sealing damaged tissue structures, such as torn vessels or open wounds. These procedures should be capable of forming an immediate closure of the damaged tissue to prevent further blood leakage and creating a permanent seal around the wound, while minimizing damage or destruction of surrounding tissue.

2. Description of the Background Art

U.S. Pat. Nos. 4,854,320 and 5,140,984 describe the use of laser emitted optical energy to heat biological tissue to a degree suitable for denaturing the tissue proteins such that the collagenous elements of the tissue form a "biological glue" to seal the tissue. PCT Application WO 94/21324 describes an applicator for introducing a fluent prepolymer liquid onto a wound. The prepolymer is then heated in situ to solidify the prepolymer, thereby creating a bond with the tissue. U.S. Pat. No. 4,034,750 describes a method for electrochemically-linking collagen membranes to the damaged collagen fibrils of an animal body. U.S. Pat. No. 5,156,613, PCT Application WO 92/14513, and copending application Ser. No. 08/231,998, assigned to the assignee of the present invention, describe a method for joining or reconstructing tissue by applying energy to a tissue site in the presence of a collagen filler material. Copending application Ser. No. 08/370,552 describes the use of an inert gas beam energy source for fusing collagen and other materials to tissue for joining or reconstructing the tissue. U.S. Pat. No. 5,071,417 describes the application of laser energy to biological materials to seal anastomoses.

SUMMARY OF THE INVENTION

The present invention provides improved methods and devices for sealing tissue to close wounds or join severed vessels. A sealant material is first heated to a suitable temperature and then applied to a wound, where it cools and sets to form a bond with the tissue. The heated sealant material flows over the wound to create an effective barrier against fluid leakage and, upon cooling, it readily adheres to the tissue to seal the wound. In addition, since high intensity energy is not applied directly to the wound, damage or destruction of neighboring tissue is minimized.

The sealant material is a biologic or biocompatible synthetic substance which will bond to underlying tissue when it has been heated to a temperature sufficient to change its physical properties and then allowed to cool on the tissue, as described in more detail hereinafter. Preferred is the use of biological materials, such as proteins and protein-containing mixtures, which will bond to underlying tissue proteins. Exemplary biological materials include collagen, gelatin, elastin, fibrinogen, fibrin, fibronectin, albumin, hyaluronic acid, chondroitin sulfate and composites and mixtures thereof.

The sealant formulation is heated to a temperature sufficient to melt the sealant, thereby forming a dispersible material which may be spread, sprayed, painted, or otherwise dispersed over the wound region. The melted sealant deposits a film onto the tissue, which on cooling forms a firm gelled state providing an immediate bond with the tissue. Preferably, the sealant will be heated to a temperature sufficient to denature surface proteins on the tissue when the sealant contacts the tissue surrounding the wound. The coagulated proteins are incorporated into the bond between the sealant and the tissue, thereby strengthening the bond.

The thermal energy to heat the sealant may be provided by a wide variety of energy sources, including electrical energy, particularly RF energy sources, microwave energy, heat energy, laser energy, ultrasonic energy, infrared energy and the like. In a specific embodiment, the sealant is conductively heated within an applicator via contact with a heating element (which is suitably coupled to the source of energy). The applicator preferably comprises a handle attached to the proximal end of an elongate shaft and an actuating mechanism, such as a plunger, for discharging the sealant from the distal end of the shaft. The sealant may be stored within a reservoir of the applicator or pre-selected amounts of sealant can be individually loaded into the shaft.

In a specific embodiment, the sealant is heated by forcibly extruding it through a heated portion of the applicator shaft. As soon as the heated sealant reaches a certain viscosity, the melted, fluid sealant will readily flow through the shaft, where it is discharged from the distal end and applied to the wound. The melted sealant can be applied to the wound in continuous sheets, layers, films, strips, patches, etc. and will generally flow together to form a coalesced layer of molten sealant (glue) on the wound. A temperature sensor, such as a thermistor(s), may be disposed within the applicator shaft for controlling and monitoring the temperature of the sealant. The applicator may also include a mechanism for preventing discharge of the sealant until it reaches a suitable temperature.

One of the advantages of the present invention is that the sealant is provided with sufficient thermal energy (i.e., temperature and heat capacity) to denature surface proteins on the tissue without affecting more than several cell layers deep. In this manner, the damage to surrounding tissue will be clinically acceptable and the sealant will suitably bond with the tissue at the target site to seal the wound and approximate the tissue.

In an exemplary embodiment, the elongate shaft of the applicator is configured for introduction through a percutaneous penetration in the patient. In this manner, the methods and devices of the present invention can be used to enhance sealing of wounds within body cavities, such as punctures or incisions in muscle tissue or the serosal tissue surrounding body organs. Since energy is not directly applied to the tissue, the methods and devices of the present invention are particularly useful for closing wounds in the tissue of body organs, such as lungs, stomach, liver, spleen, intestines, colon, and the like. The distal end of the elongate shaft may be delivered through a percutaneous penetration, such as a cannula, and positioned adjacent the target tissue within the body cavity. The sealant is then heated and discharged from the applicator onto the wound. The liquid sealant flows together and adheres to the tissue surrounding the wound, forming a bond with the tissue to seal the wound. Additional energy, e.g., from an external RF probe, may be applied to the sealant after it has been introduced onto the wound to facilitate bonding between the sealant and the underlying tissue.

DESCRIPTION OF THE SPECIFIC EMBODIMENTS

Figure 1:
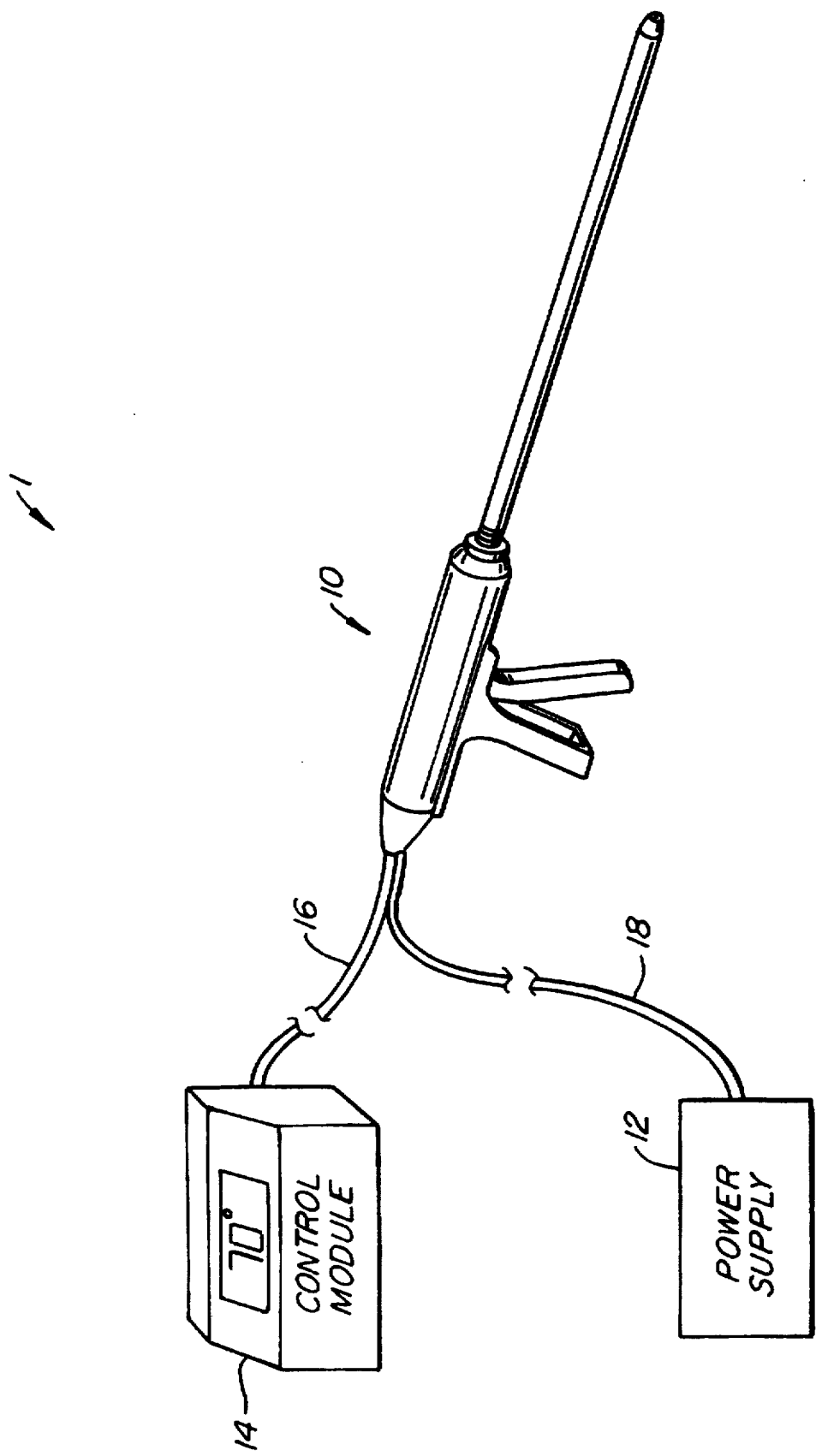
FIG. 1 is a schematic illustration of a tissue sealant system having an applicator for heating and applying sealant to damaged tissues in accordance with the principles of the present invention.

Methods and devices according to the present invention may be used for sealing severed tissue or closing wounds in virtually any body tissue, and are particularly useful for closing wounds in the tissue of body organs, such as lungs, stomach, liver, spleen, intestines, colon, esophagus, uterus, ovaries, bladder, fallopian tubes, and other tissue, such as blood vessels, tendons and muscles. The wounds may result from accidental trauma, surgical intervention, or virtually any other cause, with the methods and devices being particularly useful for the closure of surgical resections made in the lungs (lung volume reductions, bullectomies, lobectomies, segmentectomies, bronchial resections, wedge resections, pneumonectomies, pneumoreductions, etc.), in the gastrointestinal tract, (gastrectomies, intestinal/colon resection), in the liver, stomach, esophagus, uterus, ovaries, and in the spleen. In addition, the methods and devices may be used for closing suture holes in vessels, anastomosing two vessels together, bonding a skin graft to muscle tissue or tendons, reconstructing the fallopian tubes or other endoscopic or open surgical procedures. The present invention provides both secure mechanical closure of the wound and prevention or inhibition of fluid leakage, including both air leakage and liquid fluid leakage, such as blood and other bodily fluids. In addition, the sealant may provide a mechanical barrier between two tissue layers acting to prevent formation of adhesions between organs.

The present invention particularly relies on heating a sealant to a temperature sufficient to change its physical characteristics, thereby allowing the sealant to flow and to bond with the tissue. The heated, fluid sealant is applied to the region on the outer tissue surface surrounding the wound, where it flows over the inner wound surfaces and cools and sets to form suitable bonds with the tissue.

The sealant may be any natural, modified natural, or synthetic substance which has the ability to be heated into a non-solid state upon the application of energy from a suitable energy source, applied over the wound region and fused to the underlying tissue surrounding the closed. Thus, the sealant will be able to create and/or maintain a continuous film over (and sometimes penetrating into) the wound region to act both to mechanically enhance the wound closure and/or seal any perforations which may be present in the region. Such sealants should also be biocompatible (e.g., should be relatively non-toxic with low antigenicity and limited inflammatory activity) and usually (but not necessarily) will be bioabsorbable over time (e.g., being partially or completely resorbed into the underlying tissue over a period from, for example, 1 day to 90 days). Suitable synthetic materials include organic polymers which contain or have been modified to contain side groups which will bond (covalently or non-covalently) or otherwise adhere to the underlying tissue. Exemplary synthetic materials suitable for use in the present invention include organic polymers such as poly(lactic acid), poly(glycolic acid), poly (hydroxybutyrate), poly(phosphazine), polyester, and the like.

Generally, the use of natural biological polymers, and in particular biological proteins, is preferred. Suitable proteins include collagen, fibrin, fibronectin, fibrinogen, elastin, serum albumin, hemoglobin, ovalbumin, combinations thereof, and the like, and mixtures and derivatives thereof. In addition, polysaccharides, such as hyaluronic acid, chondroitin sulfate, hydroxyethyl starch, hydroxyethyl cellulose, hydroxypropyl-cellulose, carboxyethyl-cellulose, chitin/chitosan, agarose and alginate, may be used alone or in combination with other materials. Particularly preferred is the use of collagen and modified collagens, such as gelatin (which is derived from collagen in a well known manner), as described in application Ser. No. 08/303,336, filed on Sep. 9, 1994, the full disclosure of which has been previously incorporated herein by reference. A suitable medical grade fibrous collagen, for example, can be obtained from Kensey-Nash Corporation of Exton, Pa. under the brand name "Semed F". Alternatively, pharmaceutical grade gelatin, such as that manufactured by, for example, Dynagel Corporation of Calumet City, Ill. under the brand name "300 Bloom Dynagel", can be used.

Synthetic polymers can be substituted for the collagen. Suitable synthetic polymers include polyethylene glycol, polyethylene oxide, polyacrylamide, polyhydroxyethylmethacrylate, poly-vinylpyrrolidon, poly-vinyl-alcohol, polyacrylic acid and synthetic polymer films, such as polylactate and polycaprolactone. Meshes may also be used, such as metal mesh, cotton medical gauze or synthetic polymer meshes, including polyester, polypropylene, nylon and the like.

In addition to the substances described above, the sealant of the present invention may further include dyes, pigments, and the like, which may be added to improve visualization of the material during use and/or permit materials having different characteristics to be distinguished from each other. Other substances suitable for use as a component in the sealant include glycosaminoglycans, such as hyaluronic acid, dermatan sulfate, chondroitin sulfate, and heparin. Use of the glycosaminoglycans is desirable since such materials, which are anti-thrombotics, can reduce adhesion to adjacent tissues and organs. Other substances and additives may be included with the sealant for other purposes, as generally described in copending application Ser. No. 08/303,336, filed on Sep. 9, 1994, the full disclosure of which has previously been incorporated herein by reference.

The method of the present invention will utilize energy of a type and in an amount sufficient to heat the sealant to a suitable temperature for bonding with the tissue. Suitable energy sources include electrical energy, particularly RF energy sources, microwave energy, heat energy, laser energy, ultrasonic energy, and the like. Energy from the energy source will typically be applied to the sealant before it is applied to the wound. The sealant will typically be exposed to the energy for a total time from about 1/10 of a second to 5 minutes, usually from 10 seconds to 3 minutes, for material having a volume from 1 cm$^3$ to 5 cm$^3$ for endoscopic procedures and 100 to 200 cm$^3$ for open procedures. The precise timing will depend on the composition of sealant and the temperature to which the sealant will be heated, as discussed below.

The sealant is heated to a temperature sufficient to melt the sealant and is then applied to the wound in a dispersible form, preferably a liquid. The temperature at which the sealant will melt depends on the type of sealant used and the composition of the overall formulation. The preferred formulation comprises collagen at 30 to 65 parts (w/w) and polyethyleneglycol (PEG) at 8 to 20 parts (w/w) with water making up the remaining component for a total of 100 parts. With this formulation, the collagen is typically converted to gelatin (melted) by heat in the range of 40–120° C. and more preferably about 70–110° C.

The temperature to which the collagen will be heated will also depend upon the hydration level of the collagen. For example, a formula having collagen at 30 parts (w/w) will typically melt at about 50–55° C., while a formulation having collagen at 65 parts (w/w) will melt at about 75–80° C. Collagen having an extremely low water content (less than 8 parts w/w) will generally melt at temperatures greater than 100° C. Since the collagen will immediately hydrate upon contact with the hydrated tissue, it is generally preferred to use a formulation with low water content. It is also desirable, however, to have sufficient water content in the formulation so that the sealant can flow onto the wound.

The temperature to which the collagen will be subjected may depend on a variety of factors other than the melting temperature. For example, the collagen may be exposed to a much higher temperature, on the order of 150° C., for a brief period of time. In addition, heating the collagen to temperatures higher than its melting temperature, e.g., 80 to 110° C., will denature proteins at the tissue surface when the sealant is applied to the wound. These denatured proteins will have sufficent thermal energy to bond with the available proteins in the underlying tissue. It is generally desirable, however, not to exceed the above temperature ranges since the proteins in the sealant may become so denatured that they are no longer suitable as sealants and/or the sealant becomes so viscous that it is difficult to apply to the wound.

The sealant is applied to the wound after it has been sufficiently heated by the source of energy. The melted sealant can be applied to the wound so as to subsequently form continuous sheets, layers, films, strips, patches, etc., upon cooling and setting. In one embodiment, the sealant will be applied along the direction of the wound so that it penetrates directly into the wound. The tissue surrounding the wound may then be approximated and pressed together to allow adequate bonding with the sealant. Alternatively, the sealant may be applied in strips transverse to the direction of the wound. The liquid strips will flow together to form a coalesced layer of molten glue over substantially the entire open area of the wound.

When the liquid sealant is applied to the wound, it will preferably form both mechanical and chemical bonds with the tissue. Applicants believe that chemical bonds are formed by convalent bonding between the sealant and the underlying tissue proteins. Mechanical bonding occurs when the tissue elements are melted (i.e., proteins denatured) by heat transfer from the sealant. The molten tissue flows into holes and irregularities in the sealant and, when it cools and solidifies, it is trapped in these holes and irregularities so that the sealant and tissue are locked together. In addition, the melted sealant may flow into holes and crevices in the underlying tissue, which forms additional mechanical bonds when the sealant cools and solidifies.

Once the sealant has solidified, it will form a continuous sheet over the wound, thereby providing closure of the wound and inhibiting fluid leakage. For most of the materials described above, and in particular for the collagen and gelatin materials, the continuous sheet should have a thickness in the range from about 0.01 mm to 3.0 mm with a preferred thickness from 0.05 mm to 1.0 mm. Sealants having thicknesses generally greater than this range are less suitable since they display increasing stiffness.

Additional energy may be applied to the sealant after it has been introduced onto the wound to facilitate bonding the sealant to underlying tissue. Suitable energy sources include electrical energy, particularly RF energy sources, heat energy, laser energy, ultrasonic energy, and the like. Preferred are the use of RF energy sources, such as those available as electrosurgical power supplies from companies such as Valleylab, Boulder, Colo., and Birtcher Medical Systems, Irvine, Calif., employing conventional RF-applying probes. Particularly preferred are modified radio frequency energy sources which provide for a dispersed or distributed current flow from a hand-held probe to the tissue.

Energy from the energy source will typically be manually directed to the tissue using a probe connected to an external power supply. The energy may also be applied through the same applicator used to introduce the sealant onto the wound (discussed in more detail below). A more complete description of techniques for applying thermal energy to the sealant in situ can be found in co-pending application Ser. No. 08/231,998, which has been incorporated herein by reference.

FIG. 1 is an illustration of the principal components of a specific embodiment of a tissue sealing system 1 incorporating the present invention. The tissue sealing system 1 generally includes an applicator 10, a power supply 12, a control module 14 and cords 16, 18 that connect applicator 10 to control module 14 and power supply 12, respectively. Control module 12 may include microprocessors and associated electronics (e.g., negative feedback control) and displays to control and monitor the temperature of a sealant within applicator 10. Of course, the invention is not limited to an external control module and power supply. For example, suitable electronics may be incorporated into applicator 10, with power supply 12 directly connected to applicator 10, e.g. by plugging it into the wall. Alternatively, applicator 10 may include a battery operated power supply so that it is completely independent of external devices.

Figure 2:
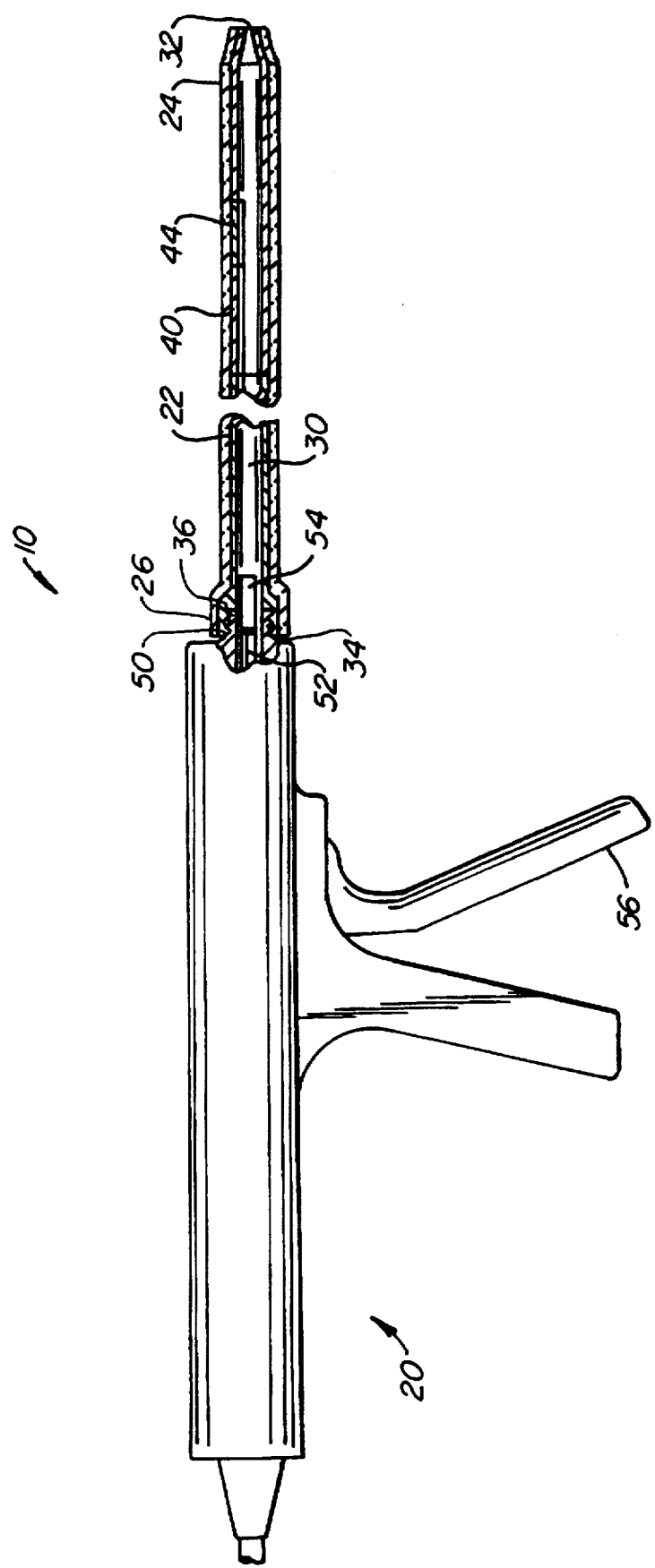
FIG. 2 is a cross-sectional side view of the applicator of FIG. 1.

Referring to FIG. 2, applicator 10 comprises a handle 20 and a hollow shaft 22 having a distal end 24 for discharging sealant and a proximal end 26 attached to handle 20. In the illustrative embodiment, shaft 22 is a rigid, stainless steel tube adapted for use in a laparoscopic environment. To this end, shaft 22 has an outer diameter in the range of 3–12 mm, usually 5–10 mm, so as to fit within a cannula having an internal diameter in the range of 5–12 mm. Shaft 22 can also be introduced directly through a percutaneous incision in the patient. Shaft 22 has a length selected to reach a target site in a body cavity, such as the lungs, and to extend sufficiently out of the body cavity to facilitate easy manipulation of applicator 10. Thus, shaft 22 should have a length of 10–50 cm and preferably 35–45 cm for laparoscopic procedures and about 12–17 cm for open procedures. It should be noted that although shaft 2 is shown as having a circular cross-sectional shape in the drawings, shaft 22 could have a rectangular, oval, channel or other cross-sectional shape. In addition, shaft 22 may comprise a flexible tube with a rigid inner guide wire.

As shown in FIG. 2, applicator 10 includes a thermally and electrically insulating sheath 29 circumscribing shaft 22. Insulating sheath 29 preferably comprises a thermally dissipating material, such as ceramic or plastic. Shaft 22 has an axial passage 30 extending from distal end 24 to proximal end 26. Distal end 24 defines a frustoconical tip 28 having an opening 32 for discharging a sealant onto a wound or incision in the patient. Preferably, opening 32 has a circular or oval shape having a maximum radial dimension of about 1 to 4 mm. Shaft 22 may also include a variety of specialized tips for applying the sealant in different patterns on the wound, such as ribbons or circular caulk beads. In addition, shaft 22 may include a blade or other cutting means (not shown) on distal end 24 for cutting various amounts of sealant as it is discharged from shaft 18.

Proximal end 26 of shaft 22 is removably coupled to handle 20 so that shaft 22 can be removed from handle 20 for sterilization, disposal, etc. In addition, shaft 22 may be removed to load the sealant into a reservoir (not shown) within handle 20 or directly into the shaft, as discussed in more detail below. In the preferred embodiment, proximal end 26 has inner threads 34 that mate with threads 36 in handle 20. However, it will be readily recognized by those in the art that shaft may be removably coupled to handle in a variety of conventional manners, such as a ball detent mechanism or an annular rib around the outside of proximal end 26 for snapping shaft 22 into handle 20.

Shaft 22 comprises a heating element 40 for applying heat to the sealant before it is discharged through distal end 24. In the illustrative embodiment, the heating element comprises a distal portion of shaft 22, which is suitable insulated from the remainder of the shaft with an insulating material, such as ceramic. Preferably, heating element 40 is made of nichrome metal and extends between 2–10 cm and more preferably between 4–6 cm. Of course, other conventional materials can be used. Heating element 40 is preferably coupled to power supply 12 via a feedback circuit (discussed below). The power supply heats the nichrome metal to a suitable temperature and sealant is heated as it is extruded through shaft 22. Alternatively, heating element 40 may be coupled to a heating mechanism, such as a conventional resistance heater, within handle 20 of applicator.

To control the temperature of the sealant, applicator 10 comprises a thermistor(s) 44 positioned near the center of heating element 40. Thermistor(s) 44 is coupled to a feedback circuit (not shown) that can be located within control module 14 or within handle 20 of applicator 10. The feedback circuit is a conventional electronic circuit designed to ensure that the temperature of sealant does not rise above a threshold level. The threshold level will be suitably selected to safeguard neighboring tissue so that the tissue damage caused by the hot sealant is clinically acceptable. The feedback circuit may be coupled to a display monitor on handle 20 or control module 14 for allowing the surgical team to monitor the temperature of the sealant. In the illustrative embodiment, the viscosity of the sealant will automatically control the lower temperature of sealant, as discussed below. However, the feedback circuit can be designed to control and monitor a lower limiting temperature as well.

Handle 20 houses an inner cylinder 50 in communication with axial passage 30 and a piston 52 mounted for reciprocal movement within cylinder 50 and passage 30. In the preferred embodiment, the sealant comprises a solid, generally cylindrical plug 54 that is loaded into passage 30 of shaft 22 from proximal end 26, as shown in FIG. 2. A trigger 56 is coupled to an actuating mechanism (not shown) within handle 40, such as a compression spring, for driving piston 52 through cylinder 50 and thereby driving sealant plug 54 through shaft 22. It should be noted that a variety of conventional actuators can be utilized to propel the sealant through shaft 22, such as hand activated plungers, gas pressure, etc.

Figure 3A:
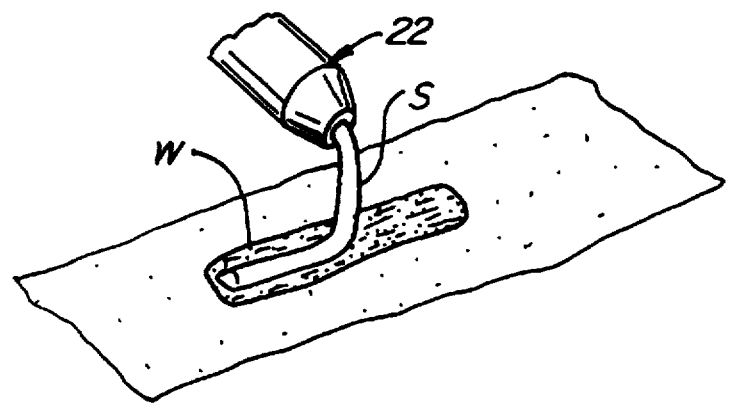
FIGS. 3A-3C are schematic views of a wound in a tissue, illustrating the method of sealing the wound according to the present invention.
Figure 3B:
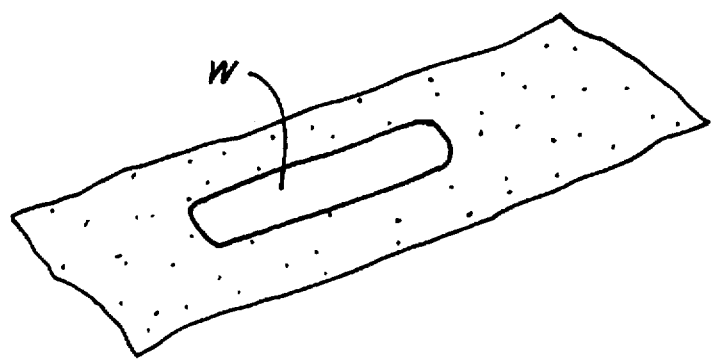

The method of the present invention will now be described in conjunction with FIGS. 2 and 3A–3C. A solid sealant plug 54, preferably comprising a mixture of collagen, PEG and water as described above, is loaded into shaft 22 and proximal end 26 of shaft 22 is mounted to handle 20 of applicator 10, as shown in FIG. 2. Power supply 12 then provides a suitable current to the resistive heater within handle 20 and heating element 40 is heated to a suitable temperature for melting sealant plug 54. As shown in FIG. 3A, distal end 24 of shaft 22 is positioned adjacent a wound W in the patient. In an endoscopic procedure, shaft 22 will first be introduced through a percutaneous penetration in the patient, such as a cannula, and guided to the target site with visual assistance from an endoscope, usually a laparoscope, or other conventional viewing device.

Once distal end 24 of shaft 22 is suitably positioned adjacent the wound W, the surgeon will actuate trigger 56 and extrude sealant plug 54 through passage 30. In its solid state, plug 54 will frictionally engage the inner walls of passage 30, making it difficult to extrude the plug through shaft 22. As plug 54 passes through heating element 40, it will be melted, and the less viscous or fluid plug 54 will then be discharged through opening 32 onto the wound W. Thermistor(s) 44 monitors the temperature of fluid plug 54 and automatically prevents further discharge of the sealant if it becomes too hot. In addition, shaft 22 may include a stop mechanism for preventing the sealant from exiting tip 28 until it reaches a threshold temperature.

Figure 3C:
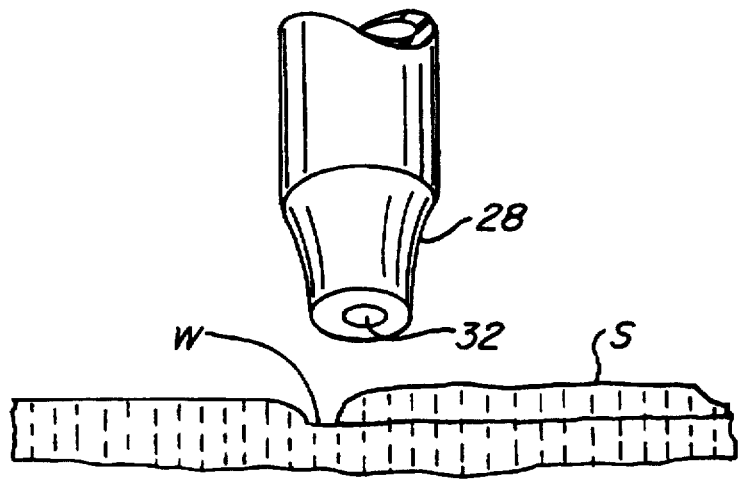

As shown in FIG. 3A, the sealant S is preferably applied generally parallel to the direction of the wound W. The wound is filled with the sealant, which begins to flow together to form a layer over the wound. The layer of glue will prevent fluid leakage through wound and it will begin to bond with the periphery tissue around wound W. As shown in FIG. 3C, the sealant melts the tissue and the molten tissue flows into holes and irregularities in the sealant. When the tissue and sealant cool and solidify, they are locked together. In addition, chemical bonds may form between the collagen sealant and the tissue proteins, as discussed above.

Although the foregoing invention has been described in detail for purposes of clarity of understanding, it will be obvious that certain modifications may be practiced within the scope of the appended claims. For example, the sealant may be applied to the wound in a variety of different manners. In one method, for example, the sealant is applied transversely across the wound W in strips. Adjacent strips of molten glue will then flow together to form the sealant layer over the wound.

What is claimed is:

1. A method for applying a sealant material to a target site on tissue, said method comprising:
providing a reservoir of the sealant material;
heating the sealant material;
applying the heated sealant material to the target site under conditions which denature surface proteins in the tissue at the target site; applying RF energy from an external probe to the sealant material; and
allowing the sealant material to cool and set at the target site.

2. The method of claim 1 wherein the sealant material is heated to a temperature from 70° C. to 110° C.

3. The method of claim 1 wherein the sealant material comprises at least one of a biologic polymer and a synthetic organic polymer.

4. The method of claim 3 wherein the sealant material is a biologic polymer comprising a protein selected from the group consisting of collagen, fibrin, fibrogen, elastin, serum albumin, fibronectin, hemoglobin, ovalbumin and combinations thereof.

5. The method of claim 3 wherein the sealant material is a synthetic organic polymer selected from the group consisting of lactic acid, glycolic acid, hydroxybutyrate, phosphazine, polyester, polyethylene glycol, polyethylene oxide, polyacrylamide, polyhydroxyethylmethacrylate, poly-vinylpyrrolidon, poly-vinyl-alcohol, polyacrylic acid, polylactate, polycaprolactone, polypropylene, nylon and combinations thereof.

6. The method of claim 3 wherein the sealant material is present at from 25% to 75% by weight in a liquid carrier.

7. The method of claim 6 wherein the sealant material comprises collagen.

8. The method of claim 6 wherein the sealant material comprises gelatin.

9. The method of claim 6 wherein the liquid carrier comprises an aqueous solution of polyethylene glycol.

10. The method of claim 1 wherein the sealant material is heated by extruding the sealant material through a heated lumen.

11. The method of claim 1 wherein the heated sealant material is applied to form a layer on a wound in tissue, the method further comprising approximating the tissue together over the wound.

12. The method of claim 1 wherein the applying step comprises substantially filling a body cavity with the sealant material.

13. The method of claim 11 wherein the wound is a surgical incision or puncture.

14. The method of claim 11 wherein the wound is present in the serosal and underlying tissue of an internal body organ.

15. The method of claim 14 wherein the internal body organ is selected from the group consisting of small and large bowels, lungs, stomach, liver, esophagus, bladder, uterus, ovaries and spleen.

16. The method of claim 11 wherein the wound is present in muscle tissue.

17. The method of claim 1 wherein the heated sealant material is applied to at least one of the ends of first and second vessels, the method further comprising pressing the ends of the first vessel to the second vessel to bond the vessels to each other.

18. The method of claim 1 wherein the heated sealant material is applied to a hole in a vessel.

19. The method of claim 1 wherein the heated sealant material is applied between a skin graft and muscle tissue.

20. The method of claim 1 wherein the heated sealant material is applied onto a fallopian tube to reconstruct said tube.

21. A method for closing a wound in tissue comprising:
housing a supply of sealant material within a reservoir of an applicator having a shaft with distal and proximal ends;
heating the sealant material;
sensing a temperature of the sealant material during the heating step;
positioning the distal end of the applicator shaft adjacent the wound;
discharging the sealant material through the distal end of the applicator shaft to apply the sealant material to the wound; and
allowing the sealant material to cool and set at the wound.

22. The method of claim 21 further including the step of introducing the distal end of the applicator shaft through a percutaneous penetration in the patient to or near a surgical incision or puncture in an internal body organ.

23. The method of claim 21 wherein the sealant material is heated by extruding the sealant material through a heated lumen near the distal end of the applicator shaft.

24. The method of claim 21 further including loading a solidified sealant plug into the introducer shaft, melting the sealant plug and discharging the melted sealant plug through the distal end of the introducer shaft.

25. The method of claim 21 further including loading a volume of sealant material into a reservoir within the applicator, the discharging step including discharging a portion of the volume of sealant material through the distal end of the applicator shaft.

26. The method of claim 21 wherein the sealant material is heated to a temperature sufficient to melt the sealant material.

27. The method of claim 21 wherein the discharging step includes extruding the melted sealant material onto the wound.

28. The method of claim 21 wherein the sealant material is heated to a temperature sufficient to denature surface proteins on the tissue when the sealant material is applied to the wound.

29. The method of claim 21 wherein the sealant material is heated to a temperature greater than 60° C.

30. The method of claim 21 wherein the sealant material is heated to a temperature from 70° C. to 110° C.

31. The method of claim 21 wherein the sealant material comprises at least one of a biologic polymer and a synthetic organic polymer.

32. The method of claim 31 wherein the sealant material comprises a protein selected from the group consisting of collagen, fibrin, fibrogen, elastin, serum albumin, fibronectin, hemoglobin, ovalbumin and combinations thereof.

33. The method of claim 31 wherein the sealant material is a synthetic organic polymer selected from the group consisting of lactic acid, glycolic acid, hydroxybutyrate, phosphazine, polyester, polyethylene glycol, polyethylene oxide, polyacrylamide, polyhydroxyethylmethacrylate, poly-vinylpyrrolidon, poly-vinyl-alcohol, polyacrylic acid, polylactate, polycaprolactone, polypropylene, nylon and combinations thereof.

34. The method of claim 31 wherein the sealant material is present at from 25% to 75% by weight in a liquid carrier.

35. The method of claim 34 wherein the sealant material comprises fibrous collagen.

36. The method of claim 34 wherein the sealant material comprises gelatin.

37. The method of claim 21 further comprising the step of applying thermal energy to the sealant material after the discharging step and before the allowing step to facilitate bonding between the sealant material and surface proteins on the tissue surrounding the wound.

38. The method of claim 37 wherein the applying thermal energy step includes applying RF energy from an external probe.

39. The method of claim 37 wherein the applying thermal energy step includes applying energy from the group consisting of electrical energy, heat energy, laser energy and ultrasonic energy.

40. A method for closing a wound in tissue comprising:
 housing a supply of sealant material within a reservoir of an applicator having a shaft with distal and proximal ends;
 heating the sealant material;
 positioning the distal end of the applicator shaft adjacent the wound;
 discharging the sealant material through the distal end of the applicator shaft to apply the sealant material to the wound;
 applying thermal energy to the sealant material after the discharging step to facilitate bonding between the sealant material and surface proteins on the tissue surrounding the wound; and
 allowing the sealant material to cool and set at the wound.

41. The method of claim 40 further including the step of introducing the distal end of the applicator shaft through a percutaneous penetration in the patient to or near a surgical incision or puncture in an internal body organ.

42. The method of claim 40 wherein the sealant material is heated by extruding the sealant material through a heated lumen near the distal end of the applicator shaft.

43. The method of claim 40 further including loading a solidified sealant plug into the introducer shaft, melting the sealant plug and discharging the melted sealant plug through the distal end of the introducer shaft.

44. The method of claim 40 further including loading a volume of sealant material into a reservoir within the applicator, the discharging step including discharging a portion of the volume of sealant material through the distal end of the applicator shaft.

45. The method of claim 40 further including sensing a temperature of the sealant material during the heating step.

46. The method of claim 40 wherein the sealant material is heated to a temperature sufficient to melt the sealant material.

47. The method of claim 40 wherein the discharging step includes extruding the melted sealant material onto the wound.

48. The method of claim 40 wherein the sealant material is heated to a temperature sufficient to denature surface proteins on the tissue when the sealant material is applied to the wound.

49. The method of claim 40 wherein the sealant material is heated to a temperature greater than 60° C.

50. The method of claim 40 wherein the sealant material is heated to a temperature from 70° C. to 110° C.

51. The method of claim 40 wherein the sealant material comprises at least one of a biologic polymer and a synthetic organic polymer.

52. The method of claim 51 wherein the sealant material comprises a protein selected from the group consisting of collagen, fibrin, fibrogen, elastin, serum albumin, fibronectin, hemoglobin, ovalbumin and combinations thereof.

53. The method of claim 51 wherein the sealant material is a synthetic organic polymer selected from the group consisting of lactic acid, glycolic acid, hydroxybutyrate, phosphazine, polyester, polyethylene glycol, polyethylene oxide, polyacrylamide, polyhydroxyethylmethacrylate, poly-vinylpyrrolidon, poly-vinyl-alcohol, polyacrylic acid, polylactate, polycaprolactone, polypropylene, nylon and combinations thereof.

54. The method of claim 51 wherein the sealant material is present at from 25% to 75% by weight in a liquid carrier.

55. The method of claim 54 wherein the sealant material comprises fibrous collagen.

56. The method of claim 54 wherein the sealant material comprises gelatin.

57. The method of claim 47 wherein the applying thermal energy step includes applying RF energy from an external probe.

58. The method of claim 47 wherein the applying thermal energy step includes applying energy from the group consisting of electrical energy, heat energy, laser energy and ultrasonic energy.

* * * * *